(12) United States Patent
Nally et al.

(10) Patent No.: US 12,324,705 B2
(45) Date of Patent: *Jun. 10, 2025

(54) HANDLE SYSTEM FOR TRANSPORT, DOCK RETENTION AND DESKTOP POSITIONING OF A PORTABLE MEDICAL DEVICE

(71) Applicant: FUJIFILM SonoSite, Inc., Bothell, WA (US)

(72) Inventors: Patrick Nally, Seattle, WA (US); Michael Pinch, Seattle, WA (US); Ken Dickenson, Bellevue, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,770

(22) Filed: Aug. 7, 2023

(65) Prior Publication Data

US 2023/0371923 A1    Nov. 23, 2023

Related U.S. Application Data

(62) Division of application No. 16/111,195, filed on Aug. 23, 2018, now Pat. No. 11,751,845.

(51) Int. Cl.
*A61B 8/00* (2006.01)

(52) U.S. Cl.
CPC .......... *A61B 8/4433* (2013.01); *A61B 8/4427* (2013.01); *A61B 8/4411* (2013.01); *A61B 8/4444* (2013.01); *A61B 8/462* (2013.01)

(58) Field of Classification Search
CPC ... A61B 8/4405; A61B 8/4411; A61B 8/4427; A61B 8/4433; A61B 8/4444; A61B 8/462
See application file for complete search history.

(56) References Cited

U.S. PATENT DOCUMENTS

| | | |
|---|---|---|
| 2005/0001413 A1 | 1/2005 | Shin |
| 2008/0249406 A1 | 10/2008 | Naruse |

(Continued)

FOREIGN PATENT DOCUMENTS

| | | |
|---|---|---|
| CN | 101732069 | 6/2010 |
| EP | 2140804 A1 | 1/2010 |

(Continued)

OTHER PUBLICATIONS

Notice of Reasons for Refusal for Japanese Patent Application No. 2021-510069, Jun. 1, 2023, 5 pages.

(Continued)

*Primary Examiner* — Christopher L Cook
(74) *Attorney, Agent, or Firm* — Womble Bond Dickinson (US) LLP

(57) ABSTRACT

Apparatuses and methods are disclosed herein for securely docking portable ultrasound imaging devices and/or other medical equipment to stand heads and other support structures. In some embodiments, a portable imaging device can include a movable carrying handle that enables the user to easily secure the imaging device to a stand head by rotating the handle to engage one or more latch mechanisms on the stand head. The user can quickly remove the imaging device from the stand head for transport to another location by disengaging the one or more latches and rotating the handle in the opposite direction. If the new location lacks a stand head or other docking structure, the user can rotate the handle downwardly to act as a stand that elevates the rear portion of the device to facilitate use on a desktop or other surface.

17 Claims, 13 Drawing Sheets

(56) References Cited

U.S. PATENT DOCUMENTS

| | | | |
|---|---|---|---|
| 2010/0000447 | A1 | 1/2010 | Song et al. |
| 2012/0044624 | A1 | 2/2012 | Hoffman |
| 2015/0094578 | A1 | 4/2015 | Ninomiya |
| 2016/0270764 | A1 | 9/2016 | Wodecki |
| 2017/0027541 | A1 | 2/2017 | Henderson |
| 2017/0281126 | A1 | 10/2017 | Meurer |
| 2018/0327013 | A1 | 11/2018 | Ferrell |
| 2019/0301899 | A1 | 10/2019 | Clos |
| 2020/0263452 | A1 | 8/2020 | Raz |

FOREIGN PATENT DOCUMENTS

| | | |
|---|---|---|
| JP | 2002368443 | 12/2002 |
| JP | 2008023007 A | 2/2008 |
| JP | 2010012226 A | 1/2010 |
| JP | 2010012227 A | 1/2010 |
| JP | 2010057887 A | 3/2010 |
| JP | 2014117360 | 6/2014 |
| KR | 100952078 | 4/2010 |
| KR | 1020130095105 | 8/2013 |

OTHER PUBLICATIONS

International Search Report and Written Opinion for PCT/US2019/047904, dated Dec. 11, 2019, 9 pages.

International Preliminary Report and Written Opinion on the Patentability of Application No. PCT/US2019/047904 Mailed Mar. 4, 2021, 6 pages.

Japanese Office Action and Search Report on the Patentability of Application No. 2021-510069 Mailed Dec. 26, 2022, 6 pages.

Decision to Grant received for Japanese Patent Application No. 2021-510069, mailed on Dec. 4, 2023, 5 pages (2 pages of English Translation and 3 pages of Original Document).

Notice of Reasons for Refusal received for Japanese Patent Application No. 2021-510069, mailed on Dec. 26, 2022, 12 pages (6 pages of English Translation and 6 pages of Original Document).

Notice of Reasons for Refusal received for Japanese Patent Application No. 2021-510069, mailed on May 30, 2023, 6 pages (3 pages of English Translation and 3 pages of Original Document).

Supplementary European search report received for European Patent Application No. 19851912.6, mailed on Mar. 21, 2022, 7 pages.

Office Action received for European Application No. 19851912.6, mailed on Mar. 7, 2024, 5 pages.

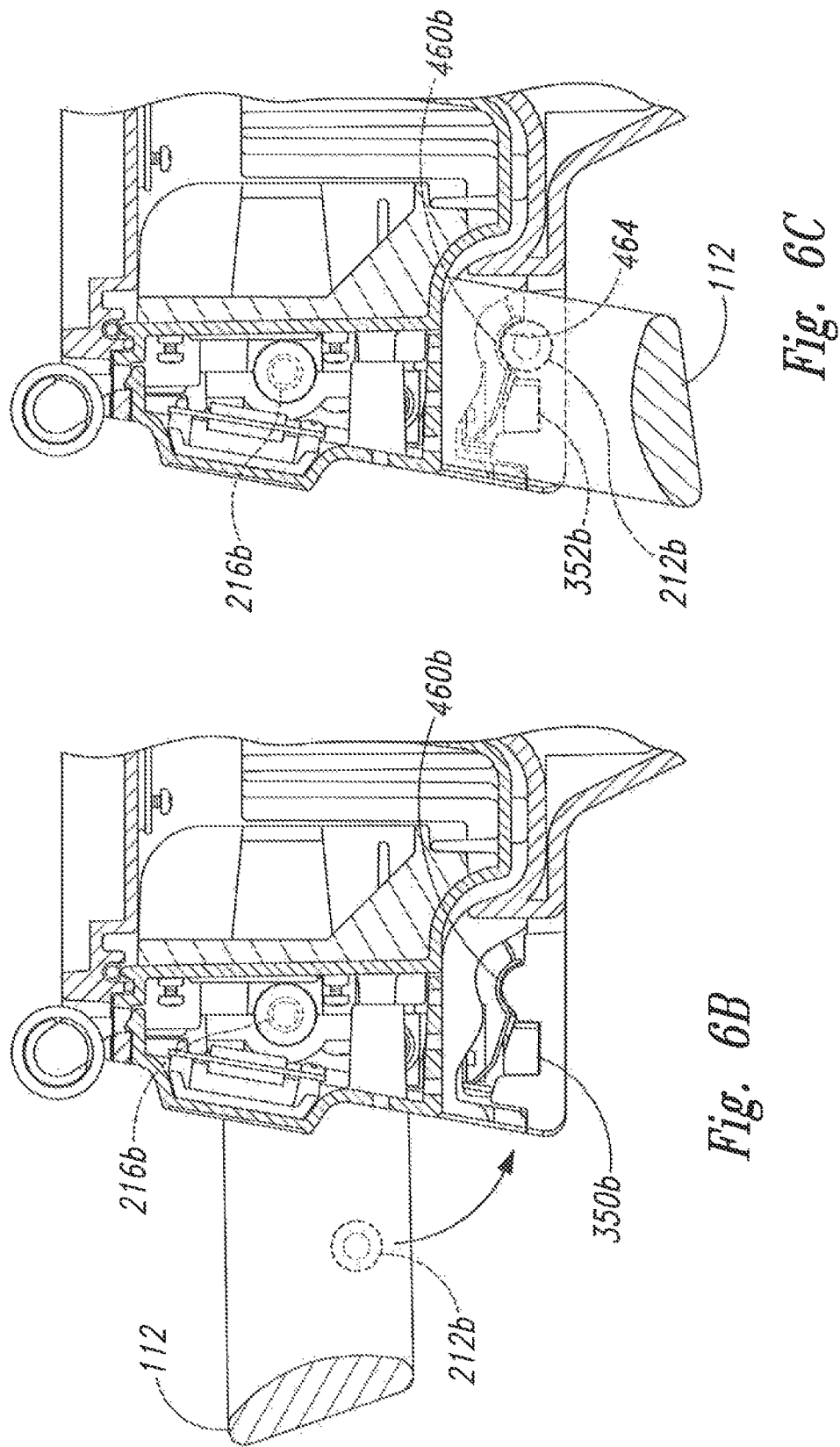

HANDLE SYSTEM FOR TRANSPORT, DOCK RETENTION AND DESKTOP POSITIONING OF A PORTABLE MEDICAL DEVICE

This application is a divisional of U.S. patent application Ser. No. 16/111,195 filed Aug. 23, 2018, which is incorporated herein by reference.

TECHNICAL FIELD

The disclosed technology relates generally to portable medical devices and systems that can be operably mounted to a stand or wall unit, and more particularly, the disclosed technology relates to a handle system for transport, dock retention, and desktop positioning of ultrasound imaging devices and other medical devices.

BACKGROUND

Portable medical equipment, such as ultrasound imaging systems, are often used while being docked to a floor-mounted stand or a wall-mounted structure, such as a "zero footprint arm." Moveable stands and zero footprint arms can provide a range of motion so that the imaging system can be advantageously positioned during, for example, a procedure in an operating room or other hospital setting. In addition, such mounting structures can also provide electrical connections for recharging the imaging device. In addition to being mountable to a stand or arm, many imaging systems are also portable and can be easily removed from the mounting structure and hand carried to other locations to perform, for example, diagnostic examinations in locations other than the typical hospital setting.

Conventional imaging devices typically include latches or similar devices on the support structure (e.g., a floor stand) to secure the imaging device to the support structure for use. One disadvantage of this approach, however, is that the location and operation of the latch may not be readily apparent to the user and, as a result, the user may inadvertently fail to properly secure the device prior to use. This raises the possibility that the device could fall or otherwise be displaced during rotation or other movement of the support structure. Accordingly, it would be advantageous to provide portable ultrasound imaging systems and other portable medical equipment that could be automatically or otherwise easily secured to the stand or other docking structure as a natural consequence of being properly mounted to the structure. Additionally, it would also be advantageous to provide such systems with the ability to be quickly and easily disconnected from the stand and hand carried to another location for use on, e.g., a desktop or other surface for diagnostic or other procedures.

BRIEF DESCRIPTION OF THE DRAWINGS

FIGS. 6B and 6C are enlarged cross-sectional side views illustrating engagement of the imaging device handle with the second latch mechanism of FIG. 5.

DETAILED DESCRIPTION

Figure 1A:
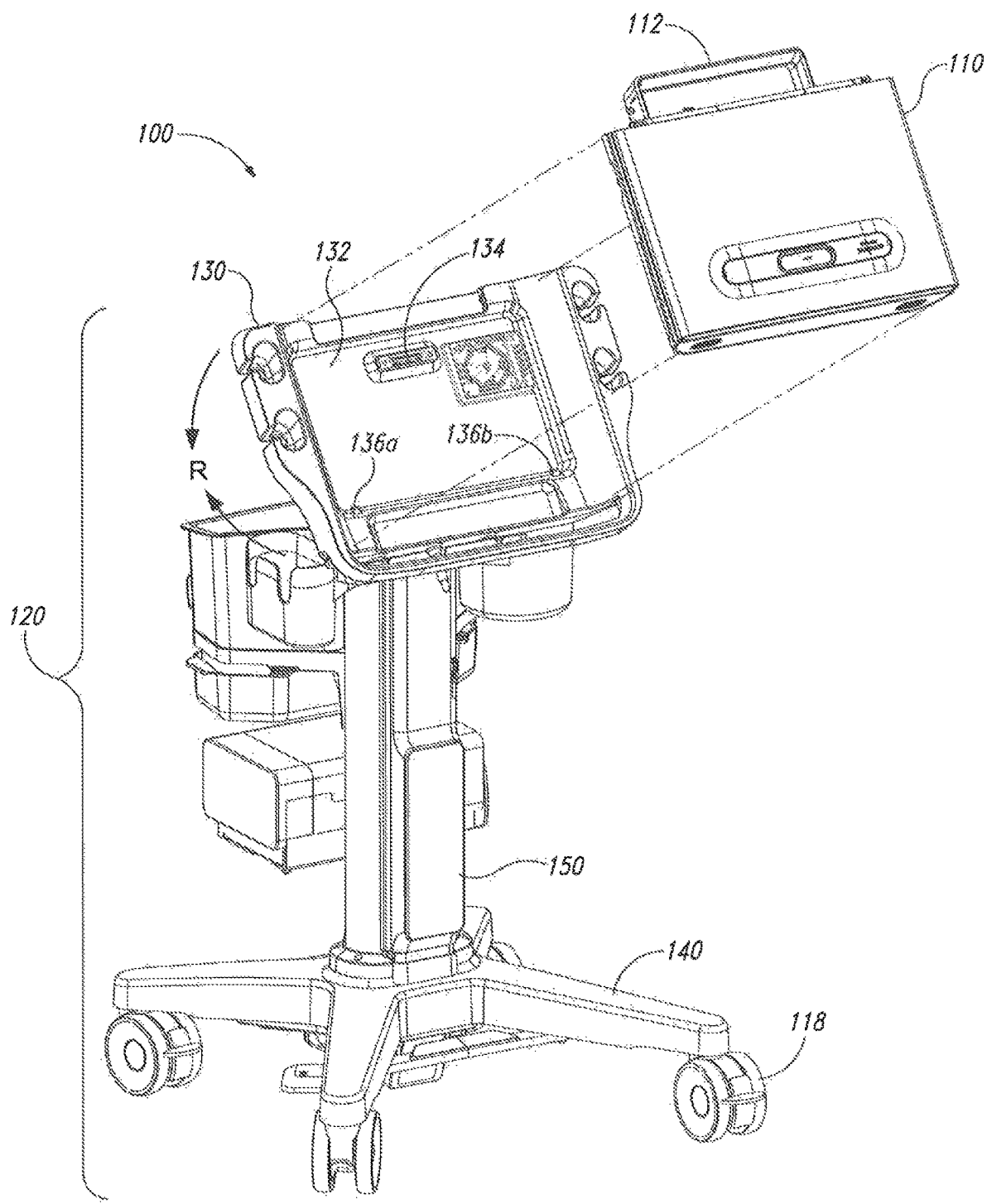
FIGS. 1A-1C are a series of isometric views of an ultrasound imaging system having a portable ultrasound imaging device and a corresponding support structure configured in accordance with an embodiment of the present technology.

The following disclosure describes various embodiments of systems and associated methods for dock retention, transport and desktop positioning of portable ultrasound imaging devices and other medical equipment. In some embodiments, the portable ultrasound imaging devices described herein include a carrying handle and other features that enable them to be easily used in different configurations and by different types of users. For example, in some configurations the device can be docked to a movable floor stand or wall-mounted arm in a hospital room or similar setting for use during a procedure. In another configuration, the device can be easily undocked and carried to another location where it is needed and placed on virtually any horizontal surface for use.

As described in greater detail below, in some embodiments the device includes a movable handle that provides much of the functionality described above. When the portable device is placed on a desktop or other flat surface, for example, the handle can be positioned to raise the rear portion of the device. In those embodiments in which the device includes a display screen pivotally connected to a control panel in a clamshell arrangement, raising the rear portion of the device in the forgoing manner can provide the user with ergonomic access to the control panel and facilitate viewing of the display screen. Additionally, in some embodiments, elevating at least the rear portion of the device above the mounting surface can create an airspace that facilitates convective cooling and improved thermal performance of the internal electrical components (e.g., CPUs, GPUs, etc.). In further embodiments, the device can also be securely mounted to a stand head or other support structure by simply repositioning (e.g., rotating) the handle to automatically engage the handle with one or more engagement features (e.g., latches) on the support structure.

Although embodiments of the present technology are described herein in the context of ultrasound imaging systems, those of ordinary skill in the art will appreciate that the disclosed technology can be used with other medical equipment (e.g., patient monitors, defibrillators, EKG machines, laptop computers, tablets, mobile devices, etc.) and/or other devices that may require securable docking systems. Accordingly, unless expressly stated otherwise the systems and methods described herein are not limited to use with ultrasound imaging systems.

Certain details are set forth in the following description and in FIGS. 1A-7 to provide a thorough understanding of various embodiments of the present technology. In other instances, well-known structures, materials, operations and/or components often associated with ultrasound imaging systems and other medical equipment are not shown or described in detail in the following disclosure to avoid unnecessarily obscuring the description of the various embodiments of the technology. Those of ordinary skill in the art will recognize, however, that the present technology can be practiced without one or more of the details set forth herein, or with other structures, methods, components, and so forth. The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the invention.

Many of the details, dimensions, angles and other features shown in the Figures are merely illustrative of particular embodiments of the disclosure. Accordingly, other embodiments can have other details, dimensions, angles and features without departing from the spirit or scope of the present invention. In addition, those of ordinary skill in the art will appreciate that further embodiments of the invention can be practiced without several of the details described below. In the Figures, identical reference numbers identify identical, or at least generally similar, elements. To facilitate the discussion of any particular element, the most significant digit or digits of any reference number generally refers to the Figure in which that element is first introduced. For example, element 110 is first introduced and discussed with reference to FIG. 1.

Figure 1B:
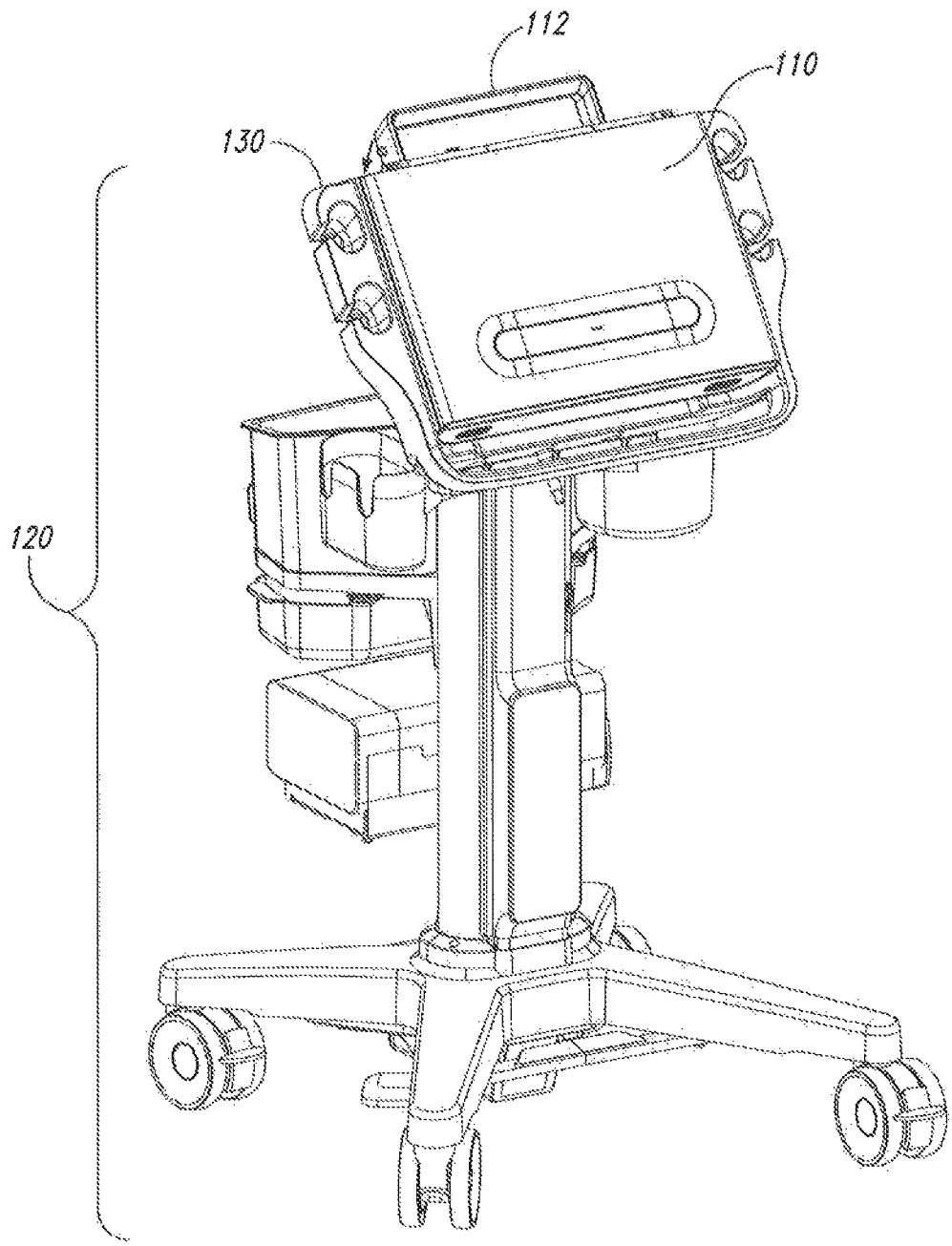
Figure 1C:
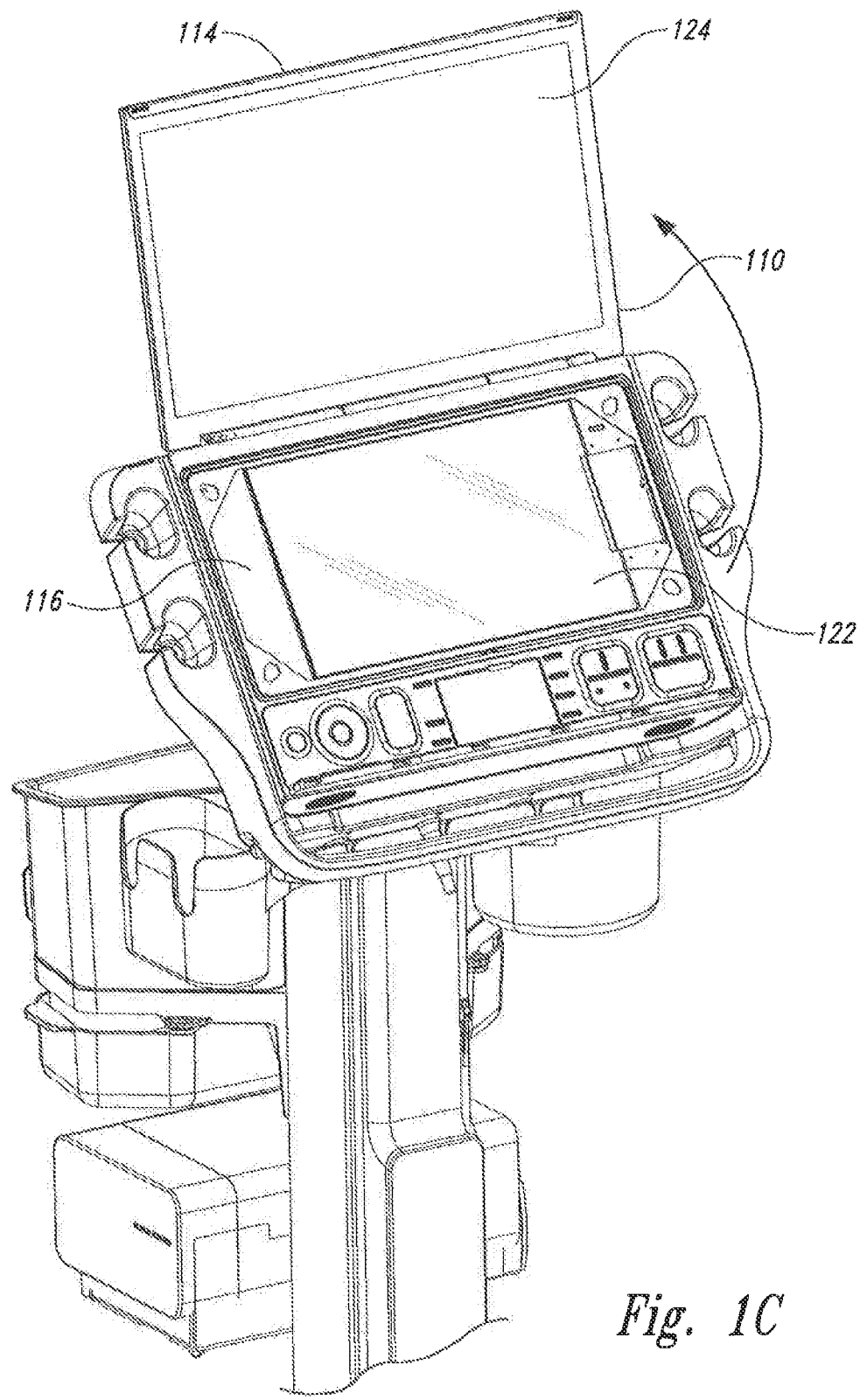

FIG. 1A is a partially exploded isometric view of an ultrasound imaging system 100 having a portable ultrasound imaging device 110 that can be securely docked to a support structure 120 in accordance with embodiments of the present technology. FIG. 1B is a similar isometric view in which the portable ultrasound imaging device 110 is docked to the support structure 120 with a corresponding device handle 112 in an un-secured or unlocked position, and FIG. 1C is a corresponding isometric view in which the portable ultrasound imaging device 110 has been opened to position a display 124 for viewing by a user. Referring first to FIG. 1A, in the illustrated embodiment the support structure 120 is a stand having a stand head 130 configured to operably receive and securely hold the portable ultrasound imaging device 110. (For ease of reference, the portable ultrasound imaging device 110 may be referred to herein as "ultrasound device 110," "device 110," and the like.) The stand head 130 is mounted to a support 150 (e.g., a vertical member) that is in turn mounted to a base 140. In the illustrated embodiment, the base 140 includes a plurality of outwardly extending legs that can include casters 118 to provide mobility to the stand 120.

In some embodiments, the stand head 130 can be pivotally coupled to the upper portion of the support 150 so that it can be positioned (e.g., manually positioned) at various angles (as shown by arrows R) to facilitate use of the device 110. In other embodiments, the stand head 130 can be fixed relative to the rest of the stand 120. In addition to the foregoing features, in some embodiments the stand 120 can also include various attachments, containers, components, etc. that may facilitate use of the imaging device 110. Such features can include, for example, power storage devices (e.g., batteries), dispensers for disposable hand wipes, gloves, etc., and/or other useful items. Although the support structure 120 is a movable floor stand, the handle systems and various embodiments thereof described herein are not limited to use with a floor stand, and accordingly can be used with virtually any type of support structure including wall mounted support structures (e.g., zero footprint arms), as well as other movable and fixed floor- or wall-mounted support structures.

In some embodiments, the stand head 130 includes a recess 132 shaped and sized to receive the device 110. The stand head 130 can also include a connector 134 positioned in the recess 132. The connector 134 can be, for example, a multi-pin connector that mates with a corresponding connector (not shown in FIG. 1A) located on a bottom surface of the device 110 to provide power to the device 110 for operation and/or recharging. The stand head 130 can also include a first tab 136a and a second tab 136b that project rearwardly from a forward edge portion of the recess 132 proximate the opposite sides thereof.

As described in greater detail below, to securely mount the imaging device 110 to the stand head 130 in accordance with some embodiments of the present technology, the handle 112 is first positioned so that it extends outwardly from the rear edge portion of the device 110 as shown in FIG. 1A. Next, the front edge portion of the device 110 is positioned in the recess 132 so that the tabs 136a, b are received in corresponding sockets (not shown in FIG. 1A) proximate the bottom surface of the imaging device 110. The imaging device 110 is then rotated downwardly toward the stand head 130 until it is received in the recess 132 as shown in FIG. 1B. In some embodiments, the recess 132 is shaped and sized to receive the imaging device 110 in proper alignment so that the connector 134 on the stand head 130 correctly mates with the corresponding connector on the lower surface of the imaging device 110. Once the imaging device 110 is mounted to the stand head 130 as shown in FIG. 1B, the handle 112 can be rotated downwardly to securely engage the handle 112 with the stand head 130 by operation of, e.g., one or latch mechanisms.

Turning next to FIG. 1C, in the illustrated embodiment the imaging device 110 includes an upper portion 114 pivotally coupled to a base or lower portion 116 in a clamshell arrangement. This arrangement enables the upper portion 114 to be rotated away from the lower portion in a conventional manner to open the imaging device 110. The lower portion 116 can include a control panel 122 having, for example, a keypad, touchscreen, and/or other functionality and controls for operation of the imaging device 110 by a user in a conventional manner, and the upper portion 114 can include a monitor or display 124 (e.g., an LCD screen) for displaying corresponding ultrasound images for viewing by the user.

Figure 2A:
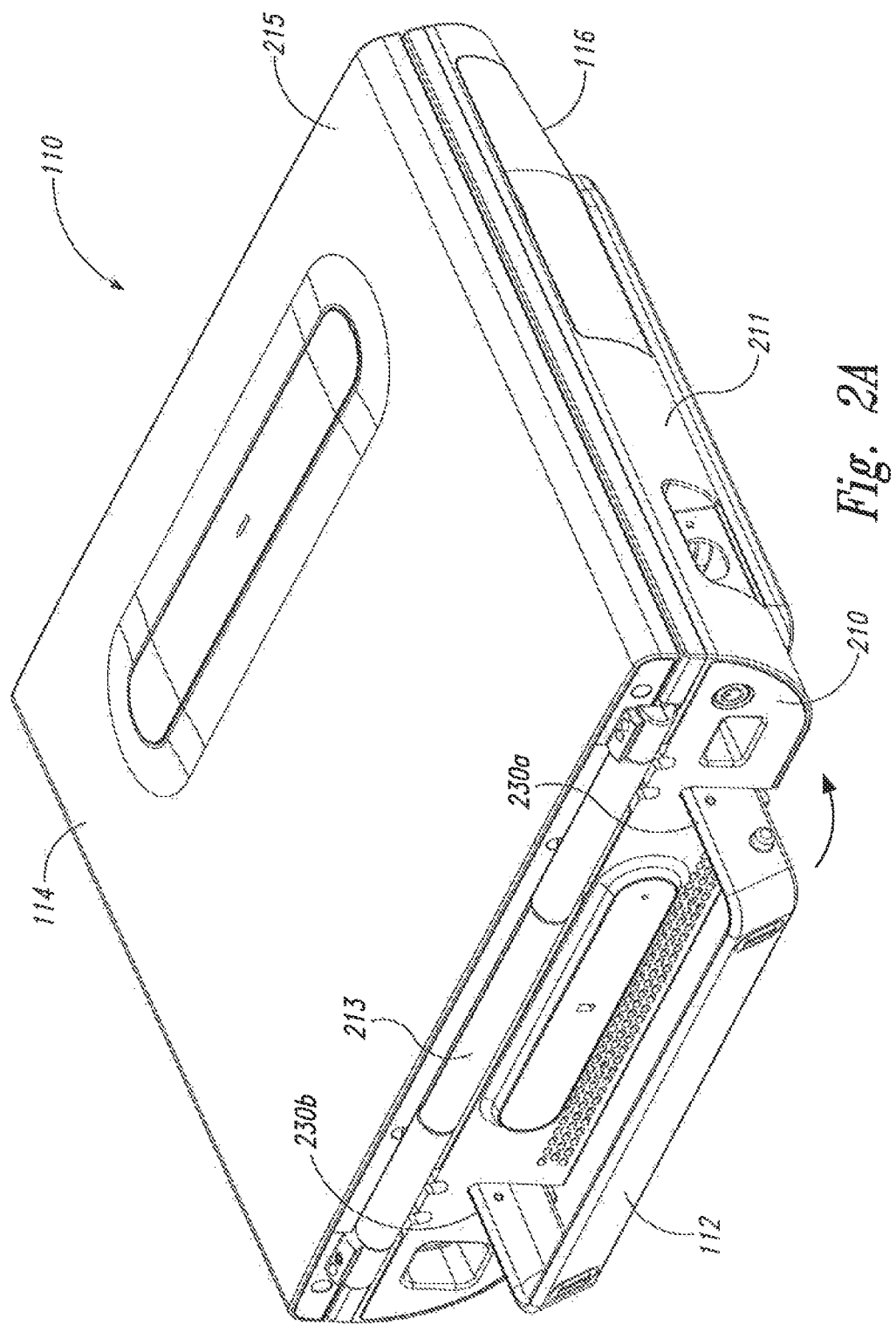
FIGS. 2A and 2B are top rear isometric views of the portable ultrasound imaging device of FIGS. 1A-1C with a handle of the device in two different positions.
Figure 2B:
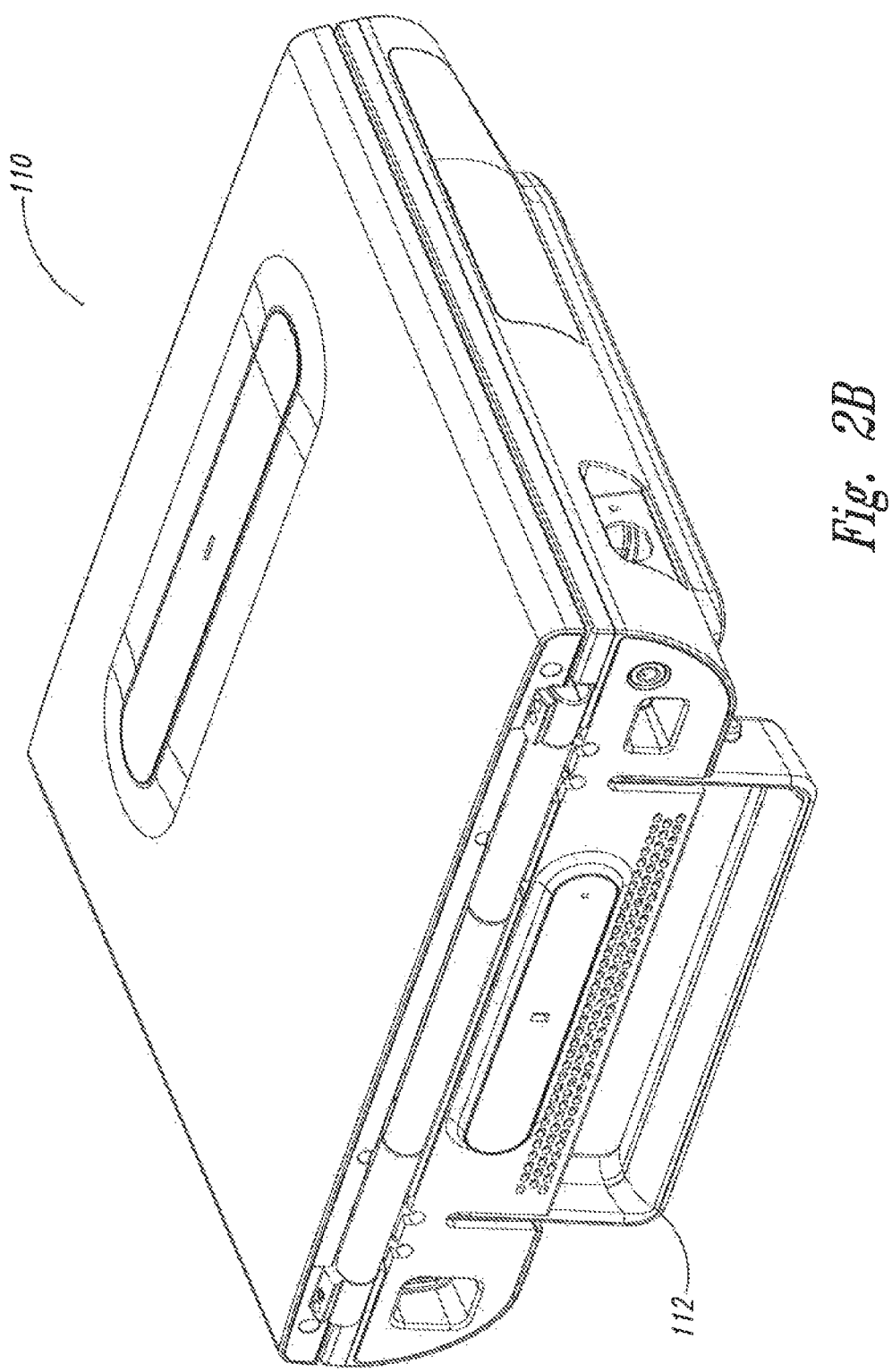

FIG. 2A is a top rear isometric view of the imaging device 110 with the handle 112 in an upper position (which may also be referred to herein as a "disengaged position"), and FIG. 2B is a similar view of the imaging device 110 with the handle 112 in a lower position (which may also be referred to herein as an "engaged position"), in accordance with embodiments of the present technology. As shown in FIG. 2A, in the illustrated embodiment the upper portion 114 includes an upper housing 215, and the lower portion 216 includes a lower housing 211 having a rear panel 210. The upper housing 215 is pivotally coupled to the lower housing 211 by means of a hinge 213 that extends transversally adjacent to the rear panel 210. The handle 112 includes a first end portion 230a and a second end portion 230b that are pivotally coupled to the lower portion 216 of the imaging device 110. In some embodiments, the handle 112 can be made from Delrin®, Tritan™ and/or other suitably strong and durable plastic materials known in the art, and the lower housing 211 and the upper housing 215 can be made from a metal casting, such as cast magnesium, aluminum, etc. In other embodiments, the handle 112 and/or the upper and lower housings 211 and 215 can be made from other suitable materials known in the art. For example, in some embodiments the handle 112 can be made from a metal casting (e.g., an aluminum casting), and the upper and lower housings 211 and 215 can be made from injection molded plastic.

A user can easily grasp the handle 112 to transport the imaging device 110 from, e.g., the stand head 130 (FIGS. 1A-1C) to another location for use on, e.g., a desktop or other horizontal surface. In some embodiments, the handle 112 can be rotated downwardly from the upper position shown in FIG. 2A to the lower position shown in FIG. 2B before operating the imaging device 110 on a horizontal surface. Setting the imaging device 110 on a desktop or other horizontal surface with the handle 112 in the lowered position provides a stand which elevates the rear portion of the imaging device 110 off the surface. This provides a space underneath the imaging device 110 that can enable air to convect heat generated by the device 110 away from the device during operation. Additionally, angling the rear portion of the imaging device 110 upwardly in the foregoing manner can also position the control panel 122 (FIG. 1C) in a favorable orientation for operation by a user. Additionally, in some embodiments the imaging device 110 can include a sensor (e.g., a contact switch, proximity switch, etc.; not shown) that detects the position of the handle 112 and provides an alarm signal if the handle 112 is not in the lower position of FIG. 2B prior to use of the imaging device 110. Such a signal can include, for example, a visual signal provided by an indicator light connected to the sensor, and/or an audible signal provided by a buzzer or other audible device. The signal could also be a text message provided via the display 114 prior to use of the imaging device 110. One benefit of such an alarm is that it can increase the likelihood that the handle 112 will be in the lower position before use of the imaging device 110 on a desktop or other surface, thereby elevating the rear portion of the device 110 for more favorable cooling during operation. Additionally, the alarm can alert the user to the fact that the handle 112 is not locked in the lower position when mounted to the stand head 130, which could result in the device 110 being inadvertently knocked off the stand head 130 in use. In yet other embodiments, the sensor could alert the user if the handle 112 is too hot for handling at any given time.

Figure 2C:
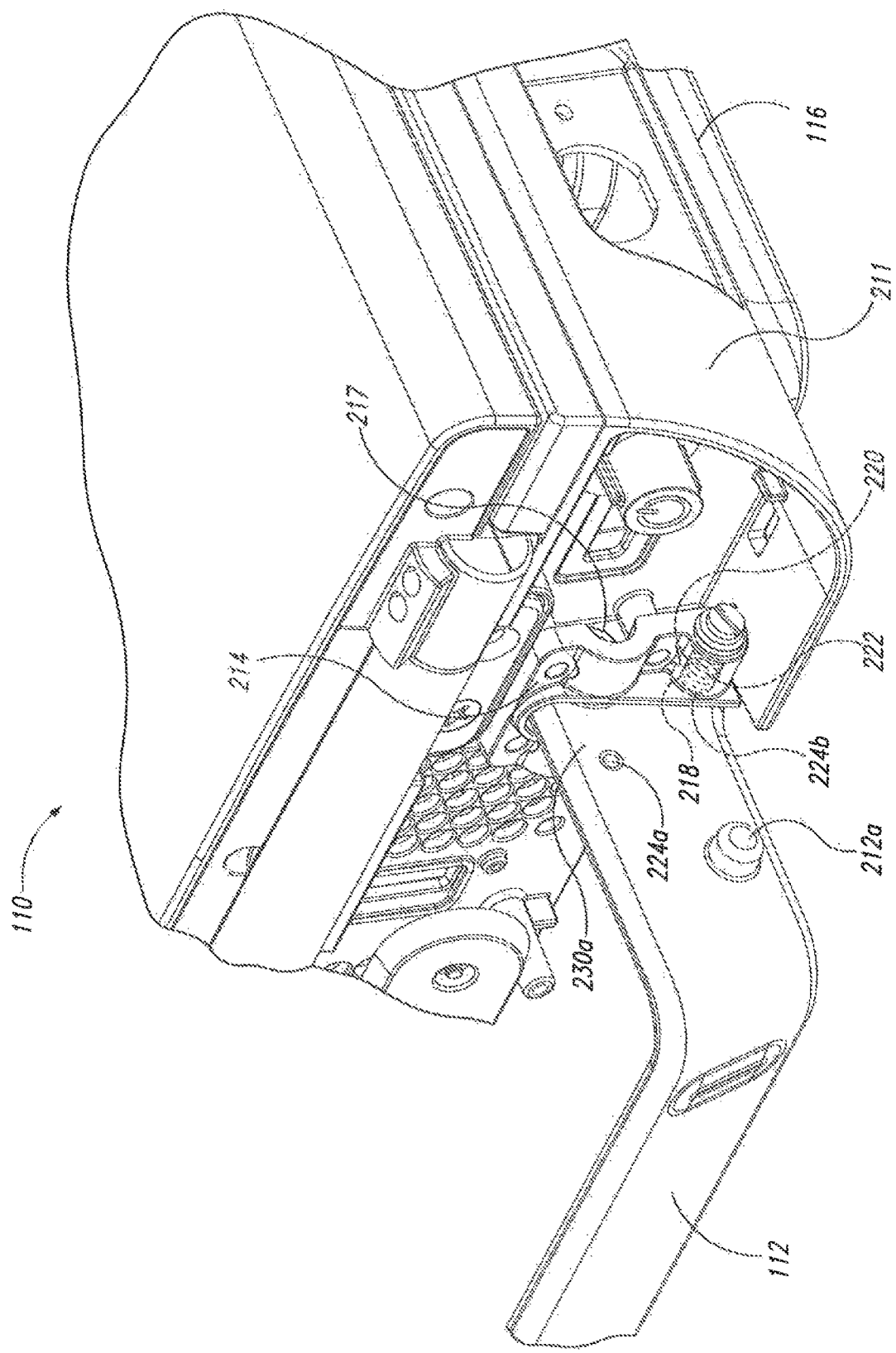
FIG. 2C is an enlarged, top rear isometric view of the device with a rear panel removed to better illustrate certain features associated with the handle.

FIG. 2C is an enlarged, top rear isometric view of a portion of the imaging device 110 with the rear panel 210 (FIG. 2A) removed from the lower housing 211 for purposes of illustrating various features associated with the handle 112. In FIG. 2C, the handle 112 is in the upper position as also shown in FIG. 2A. In the illustrated embodiment, the first end portion 230a of the handle 112 is pivotally coupled to the lower portion 116 of the imaging device 110 by a pivot pin 217 that is held in place by a hinge bracket 214. In some embodiments, the handle 112 can include a first detent 224a and second detent 224b at equivalent radial distances from the pivot pin 217. The detents 224a, b can be spherical depressions in the surface of the handle 112 that are configured to receive a ball 218 (e.g., a ball bearing) that is movably positioned in a bore 220 of the hinge bracket 214. The ball 218 is biased against the outer surface of the handle 112 by a biasing member 222 (e.g., a coil spring). In operation, the biasing member 222 urges the ball 220 into the second detent 224b to firmly hold the handle 112 in the upper position with relatively little "slop" or relative movement between the handle 112 and the lower portion 116 of the imaging device 110. However, when the user wishes to move the handle 112 to the lower position shown in the FIG. 2B, the user can apply a downward force to the handle 112 and overcome the biasing member 222, thereby causing the ball 218 to retract into the bore 220 and permit the downward rotation of the handle 112. When the handle 112 arrives at the lower position, the ball 218 drops into the first detent 224a to hold the handle 112 in this position until acted on by the user.

The opposite, second end portion 230b of the handle 112 (FIG. 2A) can be pivotally coupled to the lower portion 116 using hardware that is at least generally similar in structure and function to the components described above with reference to FIG. 2C. That is, the second end portion 230b can be pivotally coupled to the lower portion 116 by a second pivot pin 217 and a second hinge bracket 214. Additionally, the second end portion 230b can also include the ball/detent combination shown in FIG. 2C to releasably hold the handle 112 in the upper or lower position as selected by the user.

In some embodiments, at least one of the handle 112 or the stand head 130 can include an engagement feature for securing the imaging device 110 to the stand head 130 when the handle 112 is in the lower position shown in FIG. 2B. For example, in the illustrated embodiment the first end portion 230a of the handle 112 includes a first projection 212a protruding outwardly therefrom, and the second end portion 230b includes a second projection 212b (not shown in FIG. 2C) extending outwardly therefrom in the opposite direction. (The projections 212a, b can also be referred to as "nubs," "protuberances," "studs," and the like.) The projections 212a, b can have a circular cylinder shape that protrudes outwardly from the handle 112 a distance of, e.g., from about 0.1 inch to about 0.5 inch, or about 0.25 inch. As described in greater detail below, the projections 212 can be configured to engage corresponding features (e.g., latch mechanisms) on the stand head 130 when the handle is 112 is manually rotated downward to the lower position shown in FIG. 2B, to thereby "lock" the imaging device 110 to the stand head 130.

Figure 2D:
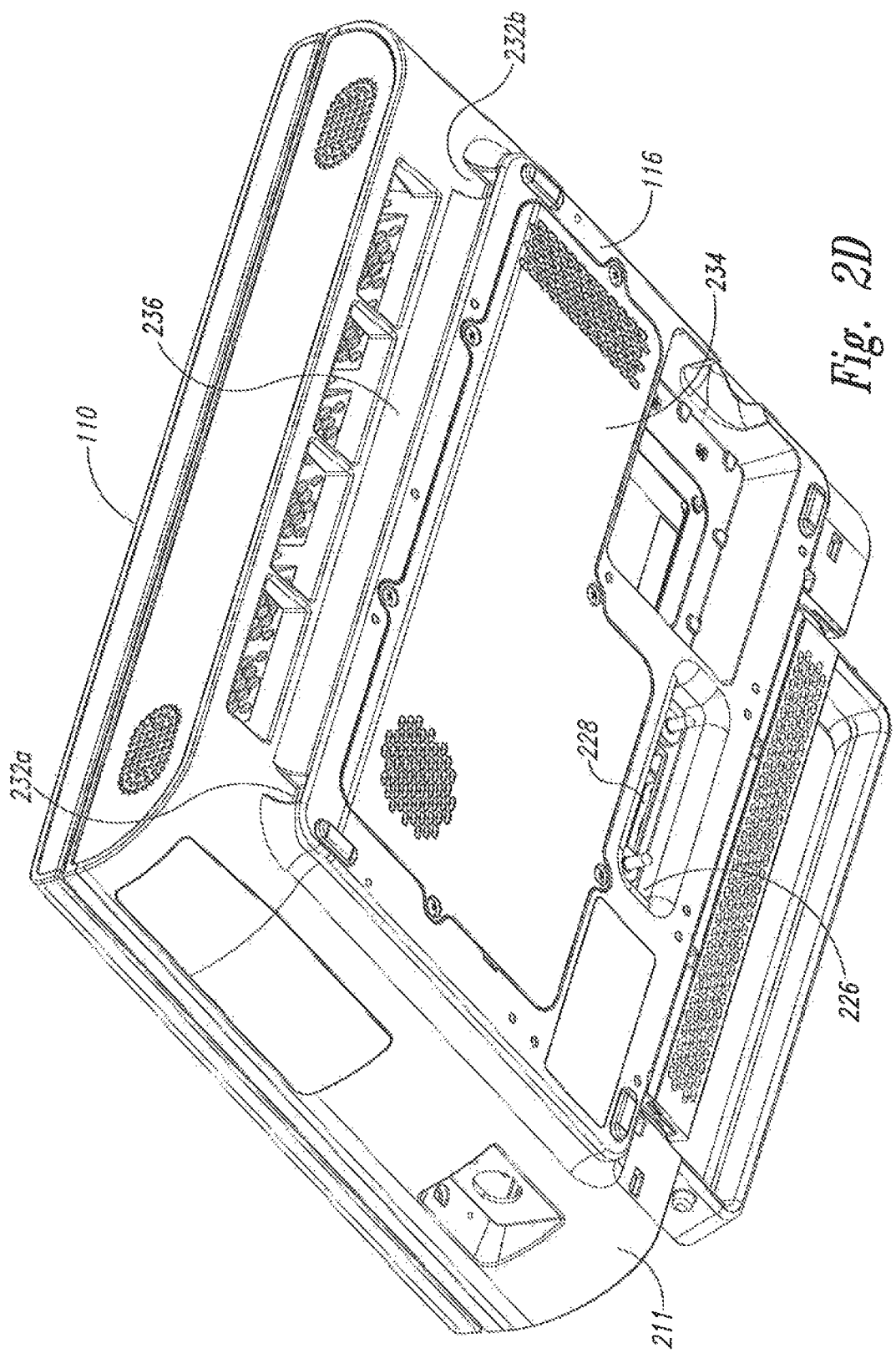
FIG. 2D is a bottom front isometric view of the device configured in accordance with an embodiment of the present technology.

FIG. 2D is a bottom front isometric view of the imaging device 110 configured in accordance with an embodiment of the present technology. In some embodiments, the lower housing 211 includes a forward surface portion 236 adjacent a bottom surface portion 234. The forward surface portion 236 includes a first socket 232a and second socket 232b positioned toward opposite sides thereof. As described in greater detail below, the sockets 232a, b are configured to receive the corresponding tabs 136a, b (FIG. 1A) on the stand head 130 when the imaging device 110 is docked to the stand head 130. The lower portion 116 of the imaging device 110 further includes a connector 228 (e.g., a multi-pin connector) positioned in a recess 226. As mentioned above with reference to FIG. 1A and described in greater detail below, the connector 228 is configured to mate with the connector 134 on the stand head 130 when the imaging device 110 is mounted to the stand head 130.

Figure 3:
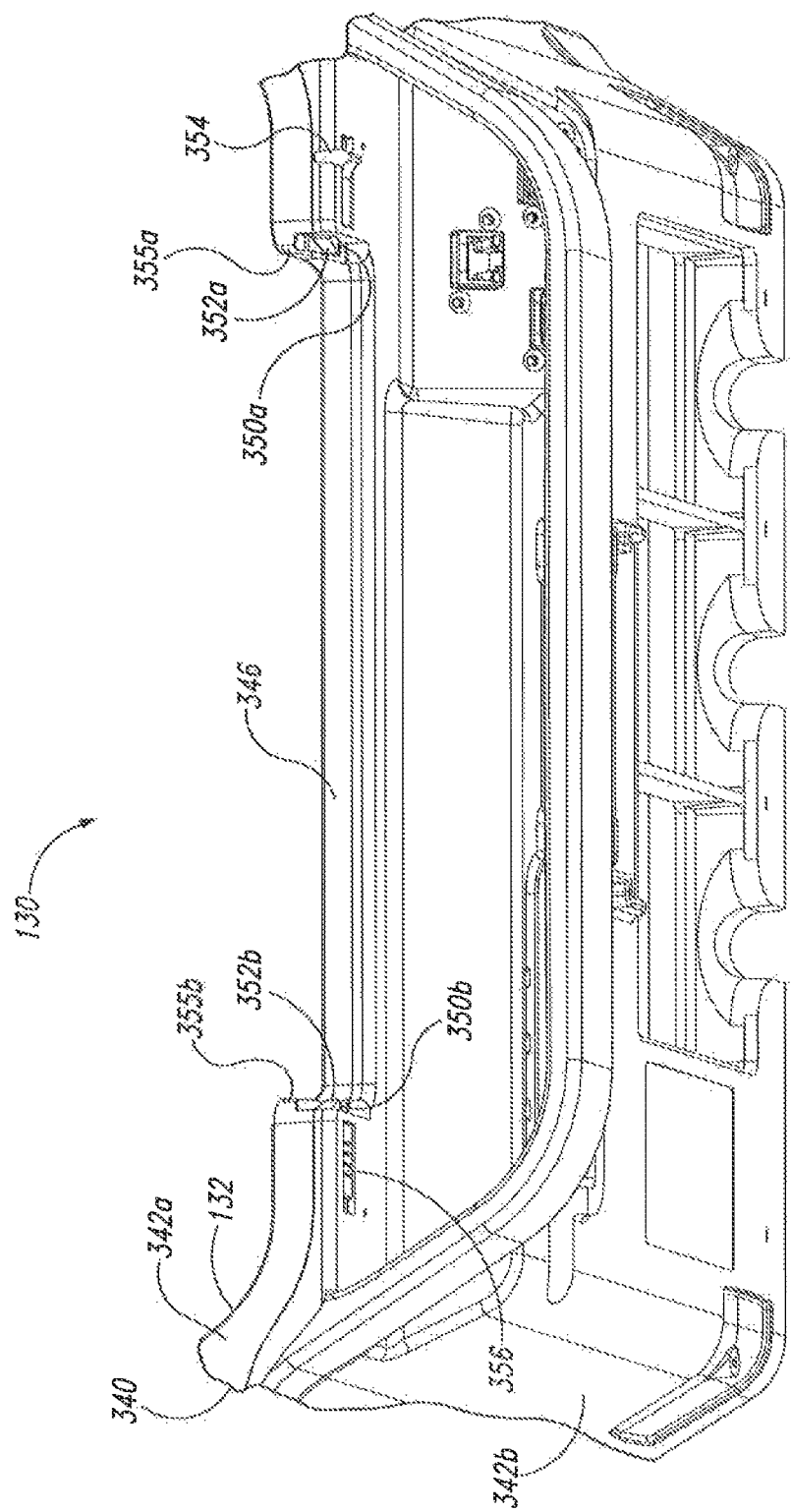
FIG. 3 is a bottom rear isometric view of a stand head from FIGS. 1A-1C configured in accordance with an embodiment of the present technology.

FIG. 3 is a bottom rear isometric view of the stand head 130 in which the stand head 130 is shown separately from the rest of the stand 120 for purposes of illustration. In the illustrated embodiment, the stand head 130 includes a housing 340 having an upper portion 342a and a lower portion 342b that are mated together. The upper and lower portions 342a, b define a rear edge portion of the stand head 130 having a cutout or recess 346. The recess 346 is configured to receive the handle 112 when the imaging device 110 is positioned in the recess 132 of the stand head 130 and the handle 112 is rotated downwardly to the lower position shown in FIG. 2B. In some embodiments, the upper and lower portions 342a, b of the housing 340 can be manufactured from cast metal, such as die cast aluminum. In other embodiments, the upper and lower portions 342a, b can be manufactured from other suitable materials known in the art, including other metals and plastic materials, such as injection molded plastic materials.

In the illustrated embodiment, the stand head 130 includes a first latch mechanism 350a positioned beneath a first edge portion 355a to one side of the recess 346, and a second latch mechanism 350b positioned beneath a second edge portion 355b to the opposite side of the recess 346. The first latch mechanism 350a includes a first latch member 352a operably coupled to a first release member 354 (e.g., a knob), and the second latch mechanism 350b similarly includes a second latch member 352b operably coupled to a second release member 356 (e.g., a slidable button). As described in greater detail below, the latch mechanisms 350a, b are configured to automatically engage the projections 212a, b, respectively, on the handle 112 (FIG. 2C) when the handle 112 is rotated downwardly to the lower position shown in FIG. 2B.

Figure 4A:
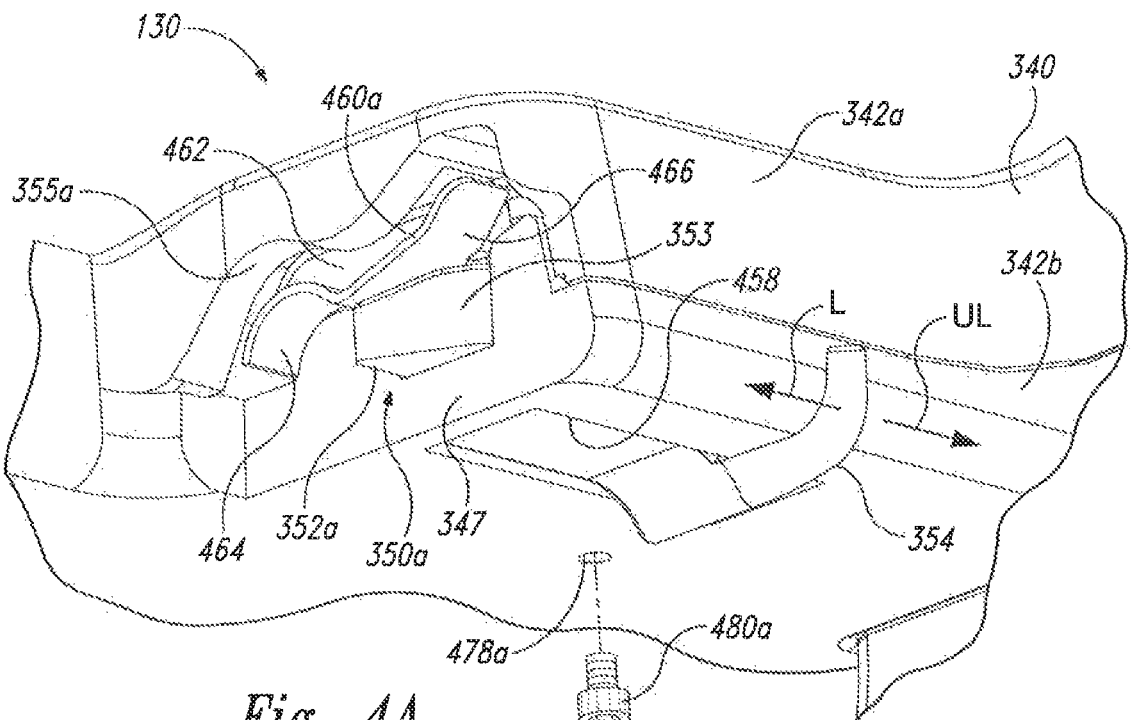
FIG. 4A is an enlarged, bottom rear isometric view of a portion of the stand head of FIG. 3 illustrating a first latch mechanism configured in accordance with an embodiment of the present technology.
Figure 4B:
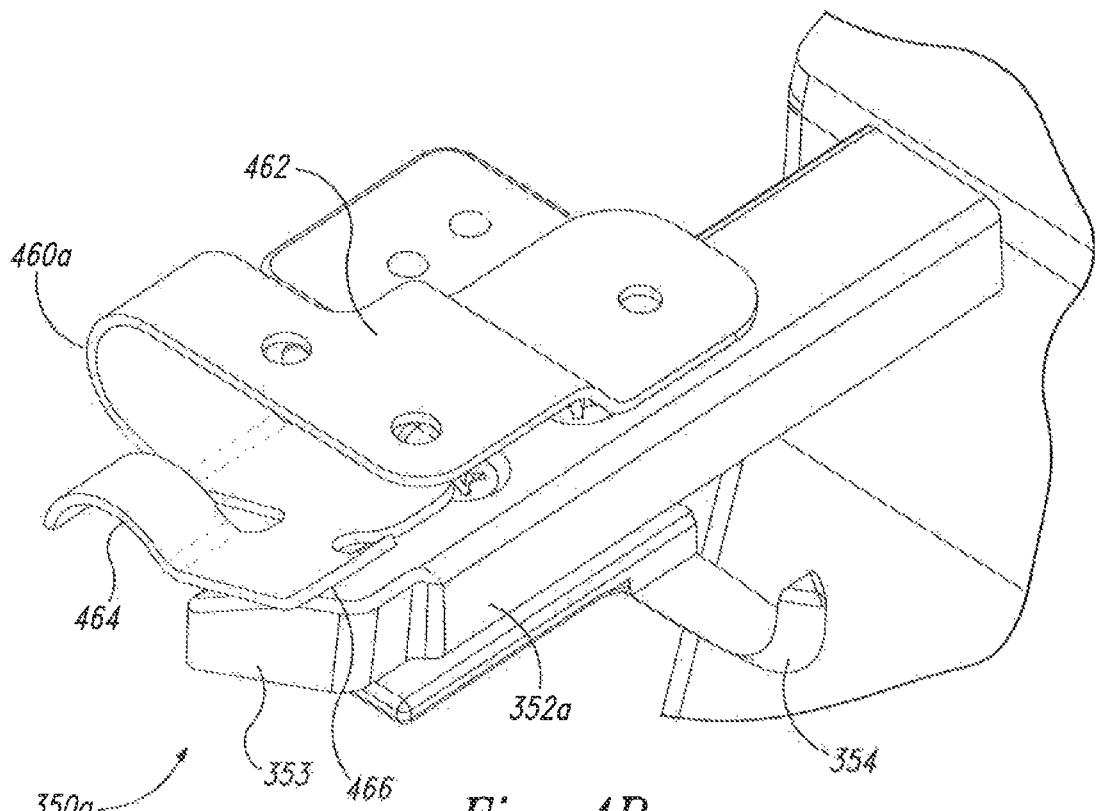
FIGS. 4B and 4C are top rear isometric and cross-sectional top rear isometric views, respectively, of the first latch mechanism with a stand head housing removed for purposes of illustration.
Figure 4C:
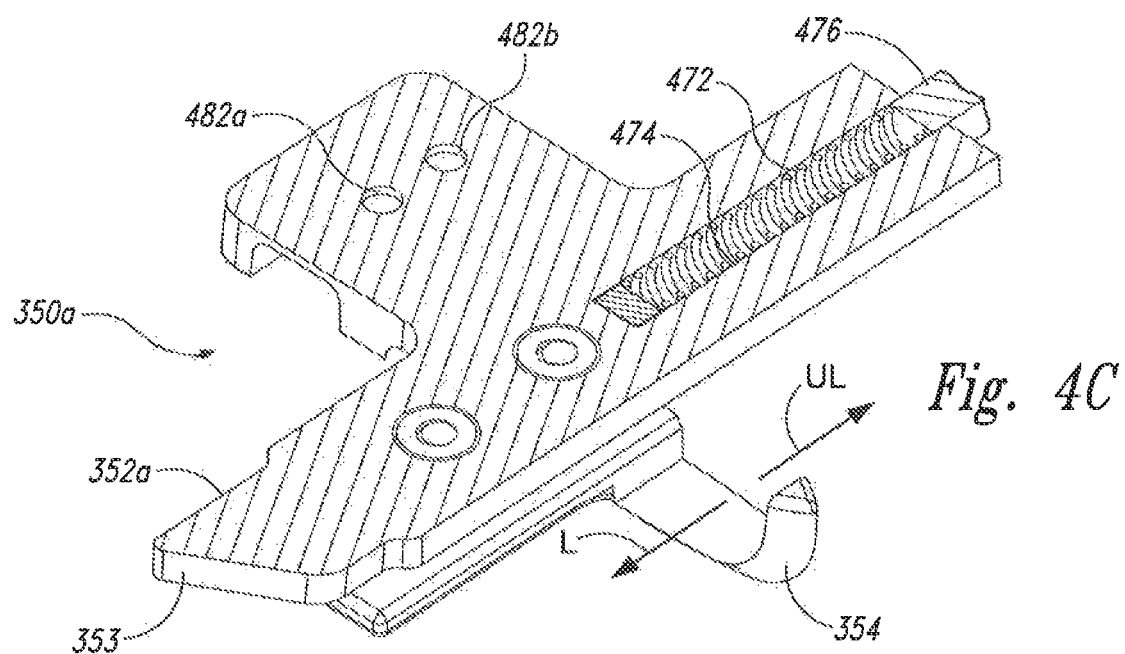

FIG. 4A is an enlarged, bottom rear isometric view of a portion of the stand head 130 illustrating the first latch mechanism 350a in more detail. FIG. 4B is a top isometric view of the first latch mechanism 350a with the stand head housing 340 removed for purposes of illustration, and FIG. 4C is a similar cross-sectional top isometric view of the first latch member 352a. Referring first to FIGS. 4A and 4C together, the first latch member 352a includes an angled surface portion 353 that protrudes outwardly from a sidewall portion 347 of the recess 346 beneath the first edge portion 355a. An opposite end portion of the first latch member 352a can include an elongate slot 474 that houses a biasing member 472 (e.g., a coil spring) that is compressed against the first latch member 352a by a stop 476 that is fixed relative to the stand head housing 340. In some embodiments, the first latch mechanism 350a can further include a locking feature. For example, the first latch member 352a can include a first fastener hole 482a (e.g., a first threaded hole) and a second fastener hole 482b (e.g., a second threaded hole). As described in greater detail below, the fastener holes 482a, b can be configured to selectively receive and engage a first fastener 480a (e.g., a screw) that is inserted through a corresponding first fastener aperture 478a in the lower portion 342b of the housing 340 to lock the first latch member 352a in either a latched position or an unlatched position.

Referring to FIGS. 4A and 4B together, in some embodiments the first latch mechanism 350a can further include a first biasing member 460a having an angled surface portion 466 and a curved (e.g., circular) surface portion 464 that is complimentary to the cross-sectional shape of the first projection 212a. The angled surface portion 466 is positioned generally above and adjacent to the angled surface portion 353 of the first latch member 352a, and the curved surface portion 464 is positioned generally behind the angled surface portion 353. The first biasing member 460a can further include a base portion 462 that is fastened or otherwise fixedly attached to the housing 340. The biasing member 460a can be manufactured from, for example, spring steel so that the angled surface portion 466 and the curved surface portion 464 resiliently deflect in response to contact by the first projection 212a (FIG. 20).

Referring next to FIGS. 4A-4C together, in operation the angled surface portion 353 of the first latch member 352a is configured to contact the first projection 212a of the handle 112 as the handle 112 is rotated downwardly from the upper position shown in FIG. 2A to the lower position shown in FIG. 2B. As the first projection 212a contacts the angled surface portion 353, it drives the first latch member 352a outwardly in the direction of arrow UL and compresses the biasing member 472. After the first projection 212a moves past the angled surface portion 353, the biasing member 472 drives the first latch member 352a back into its starting position in the direction of arrow L, and the first projection 212a moves into contact with the curved surface portion 464 of the first biasing member 460a. As the first projection 212a moves into this position, it deflects the curved surface portion 464 partially out of the way, and the resulting spring force applied by the first biasing member 460a helps to retain the first projection 212a, and hence the handle 112, in the lower position.

To release the first projection 212a and move the handle 112 into the upper position, the user can slide the first release member 354 in the direction UL. Once the handle 112 has rotated out of the recess 346 and the projection 212a is clear of the first latch member 352a, the user can release the first release member 354 and let the biasing member 472 drive first latch member 352a back in direction L to the position shown in FIG. 4A, In some embodiments, the user may wish to lock the first latch member 352a in the retracted or unlatched position so that it does not engage and secure handle 112 in the lower position. To do so, the user can slide the first release member 354 in the direction UL, and then insert the first fastener 480a through the first fastener aperture 478a and threadably engage the first fastener 480a with the first threaded hole 482a in the first latch member 352a. Doing so will hold the first latch member 352a in the retracted position so that it cannot engage or otherwise restrict rotation of the handle 112 to or from the lowered position. It should be noted, however, that the handle 112 will still be engaged with the stand head 130 when the handle 112 is in the lower position, even if the latch member 352a is locked in the unlatched position. The reason for this is that the first edge portion 355a will block the first projection 212a if the imaging device 110 initiates movement upwardly and away from the stand head 130. Conversely, the user may wish to lock the handle 112 in the lowered position to, for example, prevent the imaging device 110 from being quickly disengaged and removed from the stand head 130. To do so, the user can insert the first fastener 480a through the first fastener aperture 478a and engage the second threaded hole 482b in the first latch member 352a. Doing so will lock the first latch member 352a in the position shown in FIG. 4A and prevent a user from moving the first release member 354 in the direction UL. As a result, the user will be prevented from moving the removing the imaging device 110 from the stand head 130 until the fastener 480a is withdrawn from the second threaded hole 482b.

Figure 5:
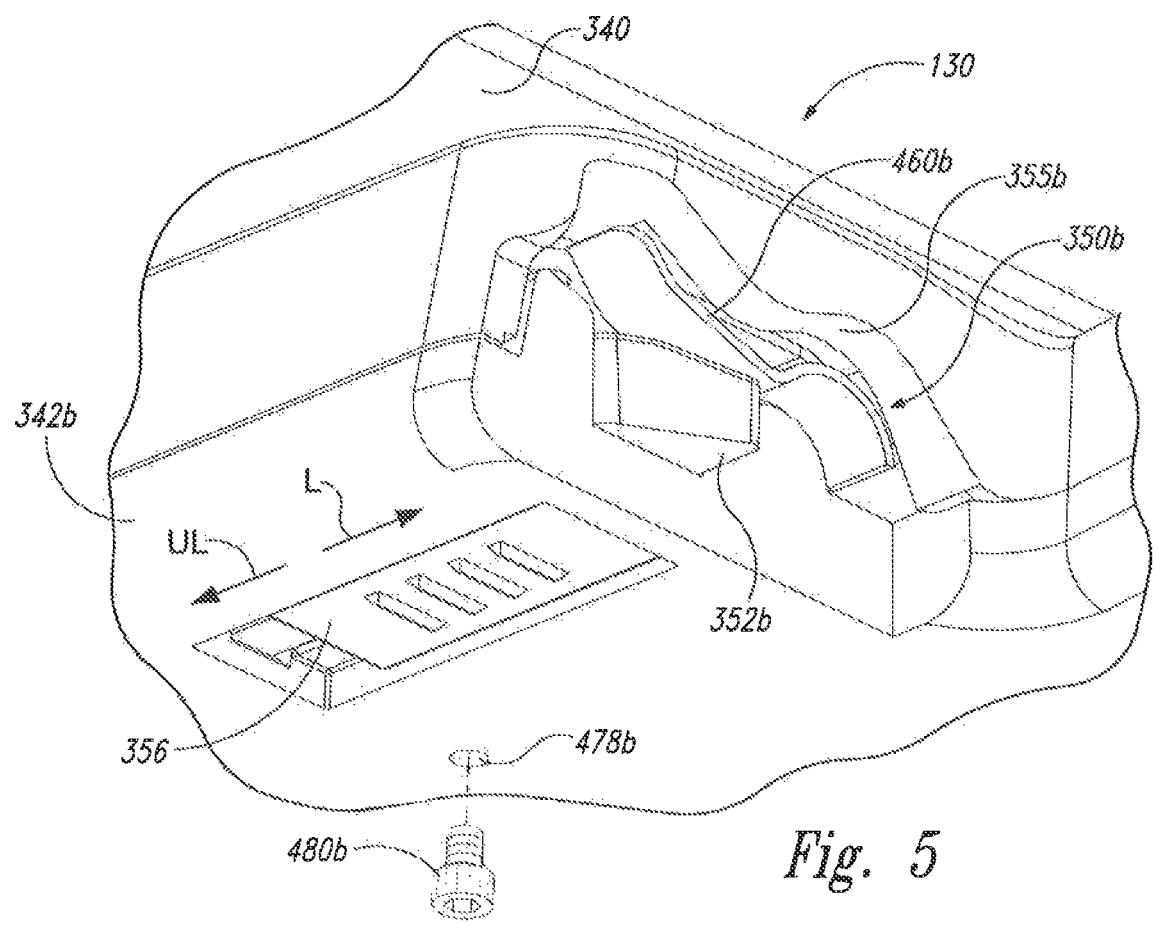
FIG. 5 is an enlarged, bottom rear isometric view of another portion of the stand head of FIG. 3 illustrating a second latch mechanism configured in accordance with an embodiment of the present technology.

FIG. 5 is a bottom rear isometric view of a portion of the stand head 130 illustrating the second latch mechanism 350b configured in accordance with an embodiment of the present technology. In some embodiments, the second latch member 352b and the second biasing member 460b can be identical, or at least generally similar in structure and function, to the first latch member 352a and the first biasing member 460a described in detail above, respectively, except that the respective parts are mirror images of each other. Otherwise, the second latch member 352b and the second biasing member 460b are structurally and functionally equivalent to the first latch member 352a and the first biasing member 460a, respectively. Additionally, the second latch mechanism 350b also includes a release feature (e.g., the second release feature 356) that is operably coupled to the second latch member 352b and functions in the same manner (or at least generally the same manner) as the first release member 354 of the first latch mechanism 350a (FIG. 4A). In some embodiments, however, the second release feature 356 can be less obvious or less conspicuous to a user than the first release member 354 (which can be, for example, a knob, handle, etc. that projects outwardly from the housing 340 as shown in FIG. 4A). For example, in the illustrated embodiment the second release member 356 is a slidable button or tab with grip features that can be manually moved in the direction of arrow UL from the position shown in FIG. 5 to retract the second latch member 352b and permit movement of the handle 112 from the lower position to the upper position.

Like the first latch mechanism 350a, in some embodiments the second latch mechanism 350b can also include a locking feature. For example, in the illustrated embodiment the second latch member 352b can be locked in either the unlatched or latched positions by inserting a second fastener 480b (e.g., a screw) through a second fastener aperture 478b in the lower portion 342b of the housing 340 and threadably engaging the fastener 480b with one of two fastener holes (not shown) in the second engagement member 352b. More specifically, to lock the second latch member 352b in the latched position shown in FIG. 5, an operator can insert the second fastener 480b through the second fastener aperture 478b and threadably engage a first adjacent fastener hole in the second engagement member 352b. If the handle 112 is in the lower position when this is done, the second projection 212b on the handle 112 will be locked in position behind the second engagement member 352b and the imaging device 110 will be locked to the stand head 130. If the user wishes to unlock the second latch mechanism 350b so that the handle 112 can be rotated upwardly and the imaging device 110 can be removed from the stand head 130, the user can do so by removing the fastener 380b and sliding the second release member 356 in the direction of arrow UL. If the user then wishes to lock the second latch mechanism 350b in the open or unlatched position, the user can do so by reinserting the second fastener 480b through the aperture 478b when the release member 356 is all the way to the left in the direction of arrow UL and engaging the second fastener 480b with a second threaded fastener hole (not shown) in the second engagement member 352b. In some embodiments, by making the second release member 356 less obvious or less conspicuous than the first release member 354, it can provide a means for an operator of the imaging system 100 to lock the imaging device 110 to the stand head 130 in a way that cannot be easily discovered by another person wishing to remove the imaging device 110 from the stand head 130.

Figure 6A:
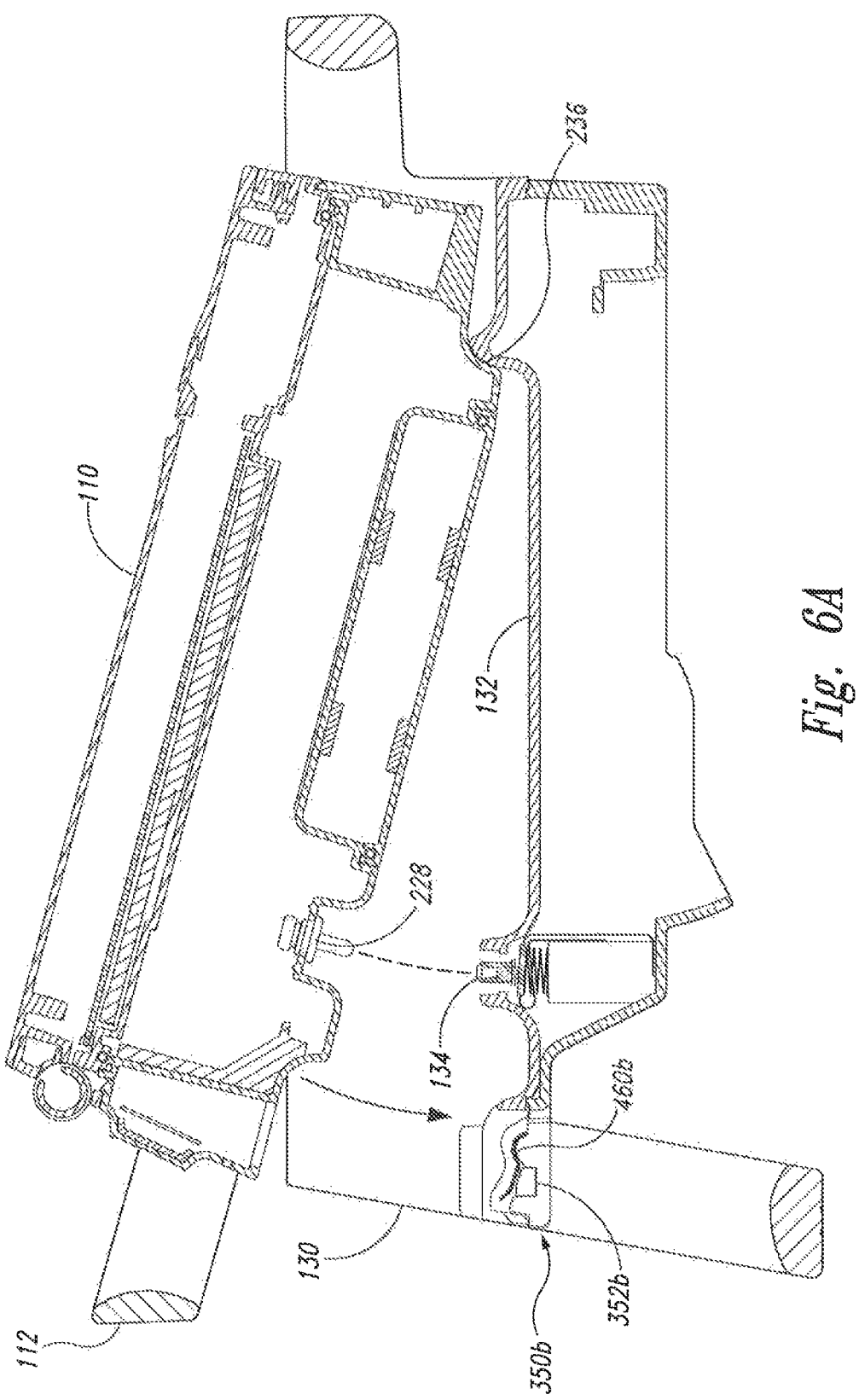
FIG. 6A is a cross-sectional side view of the portable ultrasound imaging device of FIGS. 2A-2D at an initial stage of docking to the stand head of FIGS. 3-5.
Figure 6D:
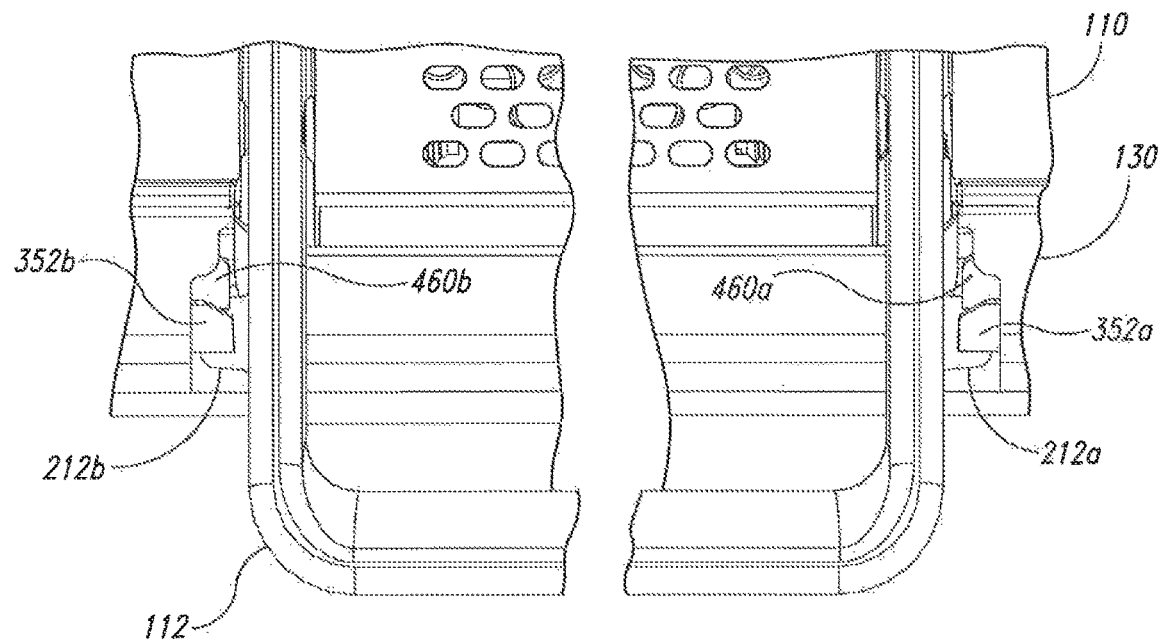
FIG. 6D is a partially cut away rear view of the imaging device handle engaged with the first and second latching mechanisms of FIGS. 3-5 in accordance with an embodiment of the present technology.

FIG. 6A is a side cross-sectional view illustrating an initial stage of mounting the imaging device 110 to the stand head 130 in accordance with an embodiment of the present technology. FIGS. 6B and 6C are enlarged side cross-sectional views illustrating engagement of the handle 112 with the second latching mechanism 350b, and FIG. 6D is a corresponding rear view of the handle 112 fully engaged with the latching mechanisms 350a, b in accordance with an embodiment of the present technology. Referring first to Figure GA, the imaging device 110 can be mounted to the stand head 130 by first inserting the tabs 136a, 136b (FIG. 1A) on the stand head 130 into the corresponding sockets 232a, b (FIG. 2D) in the lower portion 116 of the imaging device 110. Next, the imaging device 110 is rotated downwardly into the recess 132, thereby mating the electrical connector 134 on the stand head 130 to the corresponding electrical connector 228 on the imaging device 110. Referring next to FIGS. 6B and 6C together, once the imaging device 110 is fully seated in the recess 132, the user can rotate the handle 112 downwardly about the pivot pins 216a, b into the lower position shown in FIG. 6C. In some embodiments, the handle 112 is configured to rotate through an angle of from about 45 degrees to about 125 degrees, or about 85 degrees. As the handle 112 approaches the lower position, the end portions of the projections 212a, b contact the angled surfaces on the distal end portions of the corresponding latch members 352a, b and drive them outwardly in the direction of arrows UL (FIGS. 4A and 5) against the biasing force of the associated coil springs 472 (FIG. 40). This enables the projections 212a, b to move past by the latch members 352a, b as the handle 112 moves into the lower position. Once the projections 212a, b pass by the latch members 352a, b, respectively, the latch members 352a, b return inwardly to the extended or latched positions to trap the corresponding projections 212a, b and the handle 112 in the lower position, as shown in FIGS. 6C and 6D. Additionally, when the handle 112 is in this position the curved surface portions 464 of the biasing members 460a, b receive the corresponding projections 212a, b and resiliently press against them to generally hold them in place and reduce vibration of the handle 112.

Figure 7:
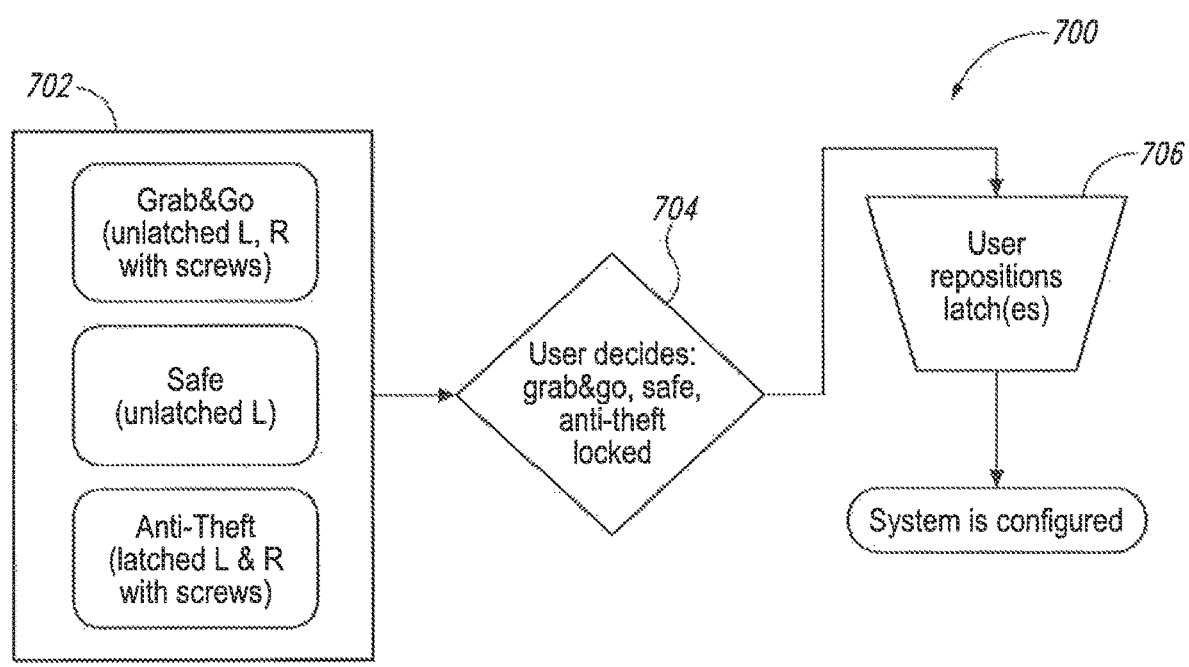
FIG. 7 is a flow diagram illustrating a method of using a portable ultrasound imaging device configured in accordance with an embodiment of the present technology.

FIG. 7 is a flow diagram of a method 700 of using the imaging device 110 and stand head 130 described in detail above. In block 702, the user can elect the manner in which they wish to use the imaging device 110. For example, the user can elect to use the imaging device 110 in a "grab and go" configuration by retracting both of the latch members 352a, b and locking them in the unlatched positions using the corresponding fasteners 480a and 480b (see e.g., FIGS. 4A and 5). This configuration enables the user to operably position the imaging device 110 on the stand head 130 and rotate the handle 112 downwardly into the lower position without engaging the latch members 352a, b. It should be noted, however, that even though the handle 112 is not engaged with latch members 352a, b in this configuration, the handle 112 is still engaged with the stand head 130 by virtue of the projections 212a, b extending underneath the corresponding edge portions 355a, b of the recess 346 in the stand head 130 (FIGS. 4A and 5). When the projections 212a, b are in this position, the corresponding edge portions 355a, b block the projections 212a, b from passing if the imaging device 110 starts moving away from the stand head 130. Thus, the imaging device 110 will still be secured to the stand head 130 and prevented from becoming dislodged in this configuration. The user can then use the imaging device 110 while it is docked to the stand head 130. But since the handle 112 will not be locked in the lowered position, the user can quickly "grab" the handle 112, rotate it to the upper position, and remove the imaging device 110 from the stand head 130 to "go" to another location where the device is needed.

Alternatively, the user may wish to use the imaging device 110 in a "safe" configuration in which the handle 112 is automatically latched to the stand head 130 when the user moves the handle 112 into the lower position. In some embodiments, the user can accomplish this by manually retracting the second latch member 352b and locking it in the unlatched position with the second fastener 480b, but not engaging the fastener 480a with the first latch member 352a so that the first latch member 352a will automatically engage the first projection 212a when the handle 112 is rotated into the lower position as described in detail above. When the handle 112 is engaged with first latch mechanism 350a in this manner, the imaging device 110 is in a "safe" configuration because it cannot be removed from the stand head 130 until the user manually disengages the handle 112 by retracting the first latch member 352a away from the first projection 212a and rotating the handle 112 upwardly as described above.

As another alternative, the user may wish to use the imaging device 110 in an "anti-theft" configuration in which it is "locked" to the stand head 130. In some embodiments, this can be accomplished by locking the first latch member 352a in the closed or latched position with the first fastener 480a (FIG. 4A), and/or locking the second latch member 352b in the latched position with the second fastener 480b (FIG. 5) as described above after the handle 112 has been engaged by the latch mechanisms 350a, b. In this configuration, the imaging device 110 cannot be removed from the stand head 130 until both fasteners 480a, b have been removed, the latch members 352a, b have been manually retracted, and the handle 112 has been rotated away from the stand head 130.

In decision block 704, the user can determine how they wish to use the imaging device 110, and in block 706 the user positions the latch mechanisms 350a, b on the stand head 130 in the appropriate way. Accordingly, it will be appreciated that the various features of the handle 112 and the latch mechanisms 350a, b described herein enable the imaging device 110 to be used in a number of different convenient configurations in accordance with the present technology.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples and embodiments of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples: alternative implementations may employ differing values or ranges.

From the foregoing, it will be appreciated that specific embodiments of the invention have been described herein for purposes of illustration, but that various modifications may be made without deviating from the spirit and scope of the various embodiments of the invention. In general, the terms used in the following claims should not be construed to limit the invention to the specific examples disclosed in the specification, unless the above Detailed Description section explicitly defines such terms. The actual scope of the invention encompasses not only the disclosed examples, but also all equivalent ways of practicing or implementing the invention under the claims. Accordingly, the invention is not limited, except as by the appended claims.

Although certain aspects of the invention are presented below in certain claim forms, the applicant contemplates the various aspects of the invention in any number of claim forms. Accordingly, the applicant reserves the right to pursue additional claims after filing this application to pursue such additional claim forms, in either this application or in a continuing application.

We claim:

1. A method of operating a portable medical device having an upper portion pivotally coupled to a lower portion in a clamshell configuration, the method comprising:
    positioning a handle of the portable medical device in a first position, the portable medical device comprising a base and the handle coupled to the base, wherein the handle comprises a first end portion, a second end portion and a handle portion between the first end portion and the second end portion;
    with the handle in the first position, operably positioning the portable medical device on a support comprising a stand head mounted to a support member, the stand head comprising a front edge support portion opposite a rear edge support portion, and a first recess between the front edge support portion and the rear edge support edge portion, the rear edge support portion comprising a second recess comprising a first edge portion and a second edge portion opposite to the first edge portion and a latch mechanism comprising an engagement member and a release member for operably coupling to the engagement member positioned beneath the first edge portion of the second recess; and
    with the base in the first recess, rotating the handle through the second recess from the first position to a second position to securely couple the handle to the stand head and prevent removal of the portable medical device from the stand head, wherein said rotating the handle from the first position to the second position actuates the engagement member to engage the handle with the latch mechanism and prevent rotation of the handle from the second position to the first position, and moving the release member from a first release member position to a second release member position retracts the engagement member to disengage the handle and permit rotation of the handle from the second position to the first position, wherein in the first position the handle portion is above the stand head and in the second position the handle portion is underneath the stand head.

2. The method of claim 1, further comprising:
    after rotating the handle from the first position to the second position, opening the portable medical device for use by rotating the upper portion away from the lower portion.

3. The method of claim 1, further comprising:
    rotating the handle from the second position to the first position to disengage
    the portable medical device from the support.

4. The method of claim 1, wherein the second recess is configured to receive the handle as the handle is moved from the first position to the second position, and wherein the stand head comprises a first latch member having an angled surface portion positioned proximate the second recess and a first biasing member coupled to the angled surface portion.

5. The method of claim 1 wherein the stand head includes a second biasing member, when the portable medical device is operably positioned on the stand head, rotating the handle from the first position to the second position automatically actuates the second biasing member to secure the handle in the second position.

6. The method of claim 1 wherein the stand head includes a release member, and wherein the method further comprises:
    moving the release member from a first release member position to a second release member position to permit rotation of the handle from the second position to the first position.

7. The method of claim 1 wherein:
    at least one of the stand head, the portable medical device, or the handle includes a latching mechanism, wherein the method further comprises: latching, by the latching mechanism, the handle to the stand head when the handle is moved from the first position to the second position to prevent the handle from being moved from the second position to the first position, and
    wherein at least one of the stand head, the portable medical device, or the handle includes a release member for the latching mechanism, wherein the method further comprises: releasing, by the release member, the latching mechanism to permit the handle to be moved from the second position to the first position.

8. The method of claim 1 wherein the upper portion includes a display, and wherein the method further comprises: rotating the upper portion away from the lower portion for viewing of the display by a user.

9. The method of claim 1:
    wherein the handle includes a first projection, and
        wherein movement of the handle from the first position to the second position causes the first projection to move a first latch member of the stand head from an extended position to a retracted position to move past the first latch member and wherein the method further comprises: allowing the first latch member to return to the extended position to block the handle from moving to the first position.

10. The method of claim 1, wherein the portable medical device includes a sensor coupled to the handle, and wherein the method further comprises: alerting, by using the sensor, a user if the handle is not in the second position prior to use of the ultrasound device.

11. The method of claim 1, wherein
    the base has a front edge base portion opposite a rear edge base portion, a display screen pivotally coupled to the base proximate the rear edge base portion; and wherein the first end portion is pivotally coupled to the base proximate the rear edge base portion, the handle including a first engagement feature protruding outwardly from the first end portion to secure the portable ultrasound device to the stand head, and wherein the stand head comprises
    at least one latch comprising a first latch member having an angled surface portion and a first biasing member coupled to the angled surface portion proximate the second recess of the rear edge support portion, wherein the method further comprises: receiving, by the first recess, the base with the handle in the first position, receiving, by the second recess, the handle when the base is positioned in the first recess and the handle is rotated from the first position to the second position;
    and automatically engaging the first end portion of the handle with the at least one latch of the stand head, wherein the angled surface portion is configured to contact the first engagement feature to drive the first latch member outwardly into a retracted position using the first biasing member of the stand head for the first engagement feature to pass the angled surface portion, and wherein after the first engagement feature passes the angled surface portion, the first biasing member is used to drive the first latch member inwardly to an extended position to trap the first engagement feature and secure the handle in the second position.

12. The method of claim 11 the method further comprising: rotating the handle about an axis that extends parallel to the rear edge base portion of the portable ultrasound device.

13. The method of claim 11 wherein:
the base includes a lower surface that defines a plane, wherein positioning the handle in the first position causes the handle to be above the plane and spaced apart from the plane by a first distance, and
wherein positioning the handle in the second position causes the handle to be below the plane and spaced apart from the plane by a second distance, greater than the first distance.

14. The ultrasound imaging system of claim 13 wherein positioning the handle in the second position causes the handle to be at an angle to the plane.

15. The method of claim 11 wherein rotating the handle from the first position to the second position includes moving the handle portion through an angle of from 45 degrees to 125 degrees.

16. The method of claim 11 wherein the support includes a support base coupled to the support member and wherein the method further comprises: positioning the support base on a floor.

17. The method of claim 11 wherein the support includes a support base coupled to the support member and wherein the method further comprises: mounting the support base to a wall.

* * * * *